United States Patent [19]

Le Goullon et al.

[11] Patent Number: 4,929,049
[45] Date of Patent: May 29, 1990

[54] FIBER OPTIC REFRACTIVE INDEX SENSOR USING A METAL CLAD

[75] Inventors: Donald Le Goullon, Tracy; Kisholoy Goswami, Walnut Creek, both of Calif.

[73] Assignee: FiberChem, Inc., Las Vegas, Nev.

[21] Appl. No.: 150,197

[22] Filed: Jan. 29, 1988

[51] Int. Cl.$^5$ ............................................. G02B 6/16
[52] U.S. Cl. ................................ 350/96.29; 350/96.34
[58] Field of Search ........................ 350/96.29–96.34, 350/301; 250/227; 65/3.11, 3.3

[56] References Cited

U.S. PATENT DOCUMENTS

| | | | |
|---|---|---|---|
| 4,418,984 | 12/1983 | Wysocki et al. | 350/96.33 |
| 4,476,870 | 10/1984 | Peterson et al. | 128/634 |
| 4,600,310 | 7/1986 | Cramp et al. | 350/96.29 X |
| 4,695,123 | 9/1987 | Chang et al. | 350/96.29 X |
| 4,781,458 | 11/1988 | Angel et al. | 356/301 |

Primary Examiner—John D. Lee
Assistant Examiner—John Ngo
Attorney, Agent, or Firm—Henry P. Sartorio

[57] ABSTRACT

A refractive index FOCS has a thin metal film clad on a fiber optic core so that transmission through the core is strongly affected by the refractive index of a surrounding solvent. The clad is made of platinum, or also of gold, rhodium or palladium. With a fluorescent tip, the changes in the fluorescent signal are a measure of the solvent refractive index. With a reflective tip, the changes in the reflected signal are measured. In a linear configuration, source and detector are placed at opposite ends of the fiber and changes in the transmitted signal are measured as a function of solvent refractive index.

21 Claims, 2 Drawing Sheets

FIBER OPTIC REFRACTIVE INDEX SENSOR USING A METAL CLAD

BACKGROUND OF THE INVENTION

The invention relates generally to fiber optic sensors, and more particularly to fiber optic sensors for measuring refractive index A fiber optic is an optical waveguide which transmits light by total internal reflection (TIR) at the core/clad interface. The critical angle $A_c$ for TIR is determined by the ratio of the refractive index $N_2$ of the clad to the refractive index $N_1$ of the core: $A_c = \sin^{-1}(N_2/N_1)$. Thus the index of the clad must be less than the core for TIR to occur.

Optical fibers have been used in a wide variety of sensors, known as "optrodes" or "fiber optic chemical sensors" (FOCS), which are designed to measure the presence of various chemical species or the value of various parameters such as pressure or temperature. In most cases a signal from a reactant, e.g. a fluorescent signal from a fluorescent dye which interacts with the desired chemical species or is affected by the desired physical parameter, is transmitted through the fiber to a detector. These sensors are generally limited by being specific to a single chemical species or physical parameter; thus each sensor is based on its own unique chemistry. U.S. application Ser. No. 046,986 filed May 6, 1987 (now U.S. Pat. No. 4,846,548) is directed to a more generalized fiber optic sensor methodology in which the principle of detection is based on how the operating characteristics of the fiber itself are modified as the result of the presence of the desired species. The use of this sensor principle allows the fabrication of many different sensors which are sensitive to particular species or even groups of species. However, it would also be desirable to have available a more general sensor which can detect a wide variety of species. Since different species usually have different refractive indexes, a single sensor which can measure refractive index would be able to detect the presence of different species. Thus such a sensor would not be species specific but would be a more universal detector.

SUMMARY OF THE INVENTION

Accordingly, it is an object of the invention to provide a fiber optic sensor which measures refractive index.

It is also an objective of the invention to provide a fiber optic sensor which can identify a wide variety of different species on the basis of different refractive indexes.

The invention is a fiber optic sensor for measuring refractive index which has a fiber optic core with a thin film metal clad. In one embodiment, the sensor has a fluorescent tip formed of a fluorescent dye immobilized on the tip of the fiber. An excitation signal is transmitted through the fiber to the tip and the fluorescent emission is detected through the fiber. In a second embodiment a silvered reflective tip is formed at the end of the fiber so that an incident signal is transmitted back. In a third embodiment, the source and detector are positioned at opposite ends of the fiber so a transmitted signal is detected. The change in refractive index of the medium surrounding the fiber changes the transmission characteristics which results in a signal change at the detector. In one embodiment, platinum (Pt) paint is applied on the side of a fiber core and is then heated with a torch to remove the organic base, leaving a thin porous platinum film. Another method of forming the clad is to paint with hydrogen hexachloroplatinate(n)hydrate and torch. In addition to platinum other metals including gold (Au), rhodium (Rh). and palladium (Pd) are suitable for the thin film metal clad.

DETAILED DESCRIPTION OF THE PREFERRED EMBODIMENTS

The invention is a fiber optic sensor with a thin metal clad on a fiber optic core which varies its transmission properties as a function of the refractive index of the surrounding medium, thus providing a measure of refractive index. In one embodiment, excitation light is transmitted through the fiber to a fluorescent tip and the returning fluorescent signal is detected. In a second embodiment, input light is reflected by a silvered reflective tip, and the reflected signal is detected. In a third embodiment, input light from a source at one end of the fiber is transmitted through the fiber and the transmitted signal is measured by a detector at the other end of the fiber.

Figure 1A:
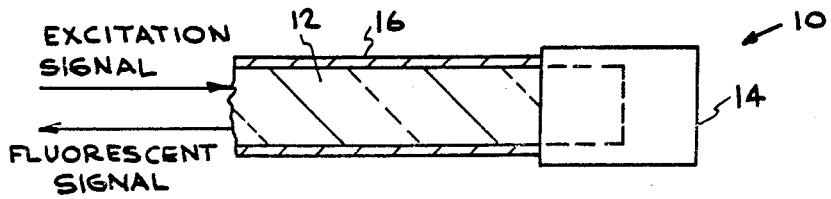
FIGS. 1A,B,C show a fiber optic sensor with thin film metal clad and fluorescent tip, reflective tip, and a linear design, respectively, for measuring refractive index.

As shown in FIG. 1A, sensor 10 has a core 12 with a fluorescent tip 14 and a thin metal clad 16. In a preferred embodiment core 12 is a silica fiber core, e.g. an Ensign Bickford MaxCore HCS fiber, with a core diameter of 400, 600 or 1000 microns and an attenuation of 10dB/km at 597$\mu$m. About one inch of the end of a fiber is stripped to the bare core, e.g. by burning off the cladding. A fluorescent chemical (dye), e.g. Rhodamine B, is attached to the distal end of the fiber core. One method of attaching the fluorescer is to close a length of shrink tubing onto the fiber core, leaving the distal end open. A grain of Rhodamine B is placed in the open end of the shrink tubing which is then filled with methanol or other solvent to dissolve the dye. A small drop of cyanoacrylate ester (super glue) is then placed on the open end and the tip is heated, e.g. with a hot air gun, to seal the open end to form a fluorescence sack. Optical adhesive, e.g. Norland #61, is then coated on the outside of the entire fluorescence sack surface of the shrink tubing to completely seal the fluorescer.

Figure 1B:
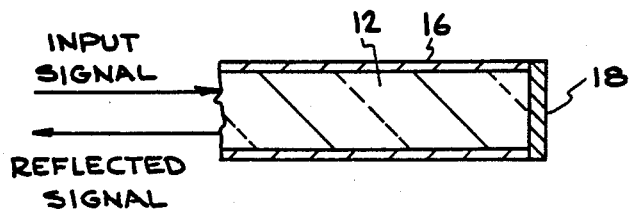
Figure 1C:
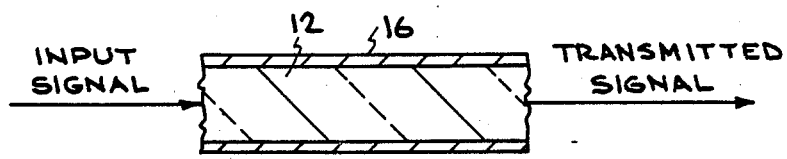

In the embodiment of FIG. 1B a reflective tip 18 is formed onto the end of fiber optic core 12 with its thin film metal clad 16. In the linear (dual end) embodiment of FIG. 1C, a portion of fiber optic core is clad with thin metal film 16.

In order for the core to transmit light efficiently, the core must be clad with a material of lower refractive index than the core. With the clad removed, light is transmitted very inefficiently. As the core is placed into various solvents, the light is transmitted with an efficiency which depends on the refractive index of the solvent. The solvent, in essence, becomes the clad. The lower the refractive index of the solvent, the more light is transmitted through the core.

In accordance with the invention, a thin metal clad on the fiber core enhances the change in light transmission of the core as a function of the refractive index of the surrounding solvent. Thus the thin metal clad on the core amplifies the effect and provides greater sensitivity, producing a simple, rugged and practical refractive index sensor. In the first embodiment platinum (Pt) paint (Engelhard #A4338 platinum ink) was placed on the side of the bare core. The organic components base of the paint was removed by burning off with a torch to leave a thin shiny Pt coat on the fiber core. Alternatively the core is painted with hydrogen hexachloroplatinate(N)hydrate and torched. Thin films of other materials such as gold (Au), rhodium (Rh) and palladium (Pd) may also be formed.

When the Pt coated core was placed into various solvents, the sensitivity was markedly increased over the core alone. Thus a thin film of Pt or other metals including Au, Rh and Pd, can be applied to the side of the fiber core by painting, sputtering, or other suitable method such as plating from solution. The layer is heated, if necessary, to remove organic components. A very thin film, e.g. a few monolayers or less, is desired because the evanescent wave in the fiber core only penetrates a short depth into the clad. The thickness of the thin film is important; an effective thickness allows the transmission of the fiber core to be strongly affected by the refractive index of the surrounding solvent. The thickness should be less than the penetration depth of the evanescent wave propagating through the fiber core so the surrounding solvent can affect transmission.

Figure 2:
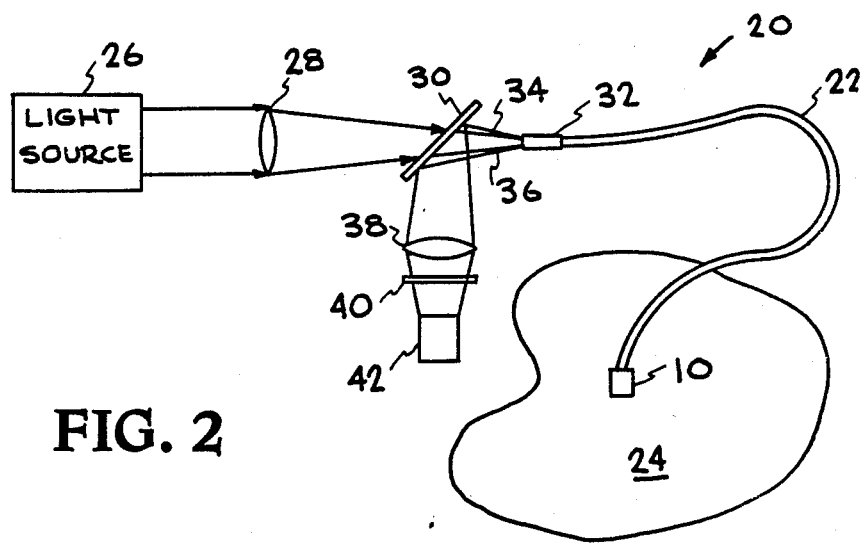
FIG. 2 is sensor system for measuring refractive index of a sample.

A sensor system 20 is illustrated in FIG. 2 A sensor 10, as shown in FIG. 1A, is formed on one end of an optical fiber 22 and placed in a sampling region 24. Light from a light source 26. e.g. an argon laser at 488nm producing 5mW power, is focused by lens 28 through dichroic mirror 30 and into the opposite end 32 of fiber optic 22. This excitation light 34 is transmitted by the fiber to sensor 10 to excite the fluorescer The returning fluorescent signal 36 is reflected at dichroic mirror 30 and passes through lens 38 and filter 40 into detector 42. The signal received by detector 42 is a measure of the refractive index of the solvent in sample region 24. Similar systems can be formed with the sensor of FIG. 1B where the reflected signal is measured instead of a fluorescent signal, or with the sensor of FIG. 1C where the detector is placed at the opposite end of the fiber from the source and the transmitted signal is measured.

Figure 3:
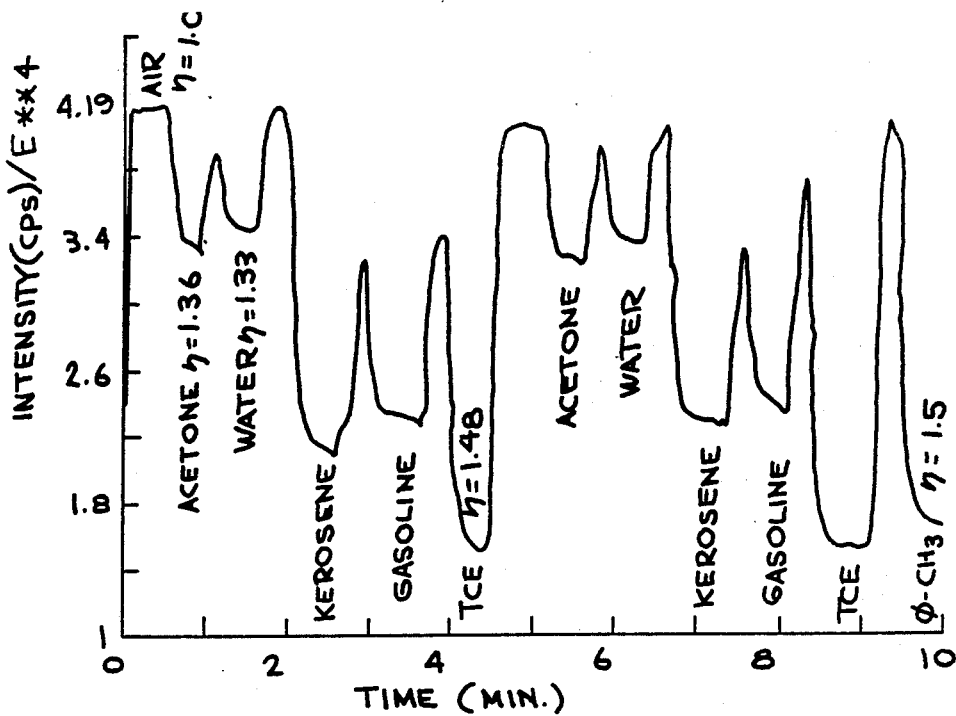
FIG. 3 is a graph of signal intensity as a function of solvent refractive index for a series of different solvents.
Figure 4:
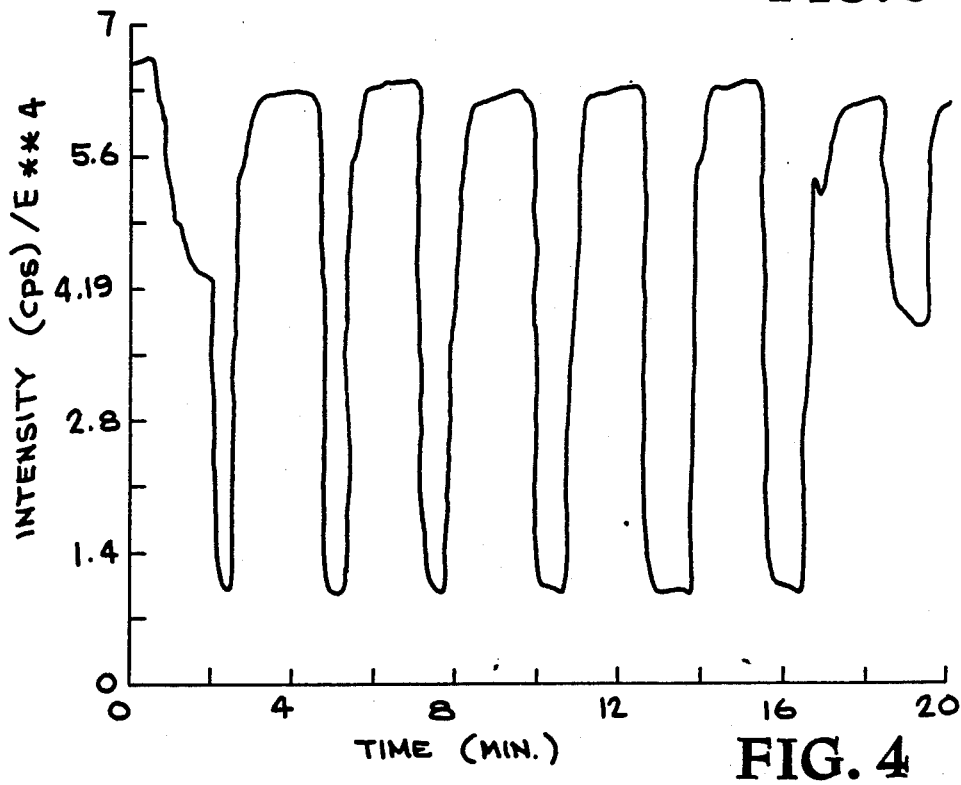
FIG. 4 is a graph of the response of a gasoline sensor.

FIG. 3 illustrates the response of a general refractive index FOCS according to the invention where a number of different solvents are sequentially flowed over the sensor. The intensity variations at the detector clearly differentiate between different solvents (different refractive indexes). The sensor quickly recovers from one sample solvent to another and the measurements are reproducible, i.e. a similar detector intensity is produced by repeating a solvent. FIG. 4 shows the response of a refractive index sensor to repetitive samples of gasoline.

Changes and modifications in the specifically described embodiments can be carried out without departing from the scope of the invention which is intended to be limited only by the scope of the appended claims

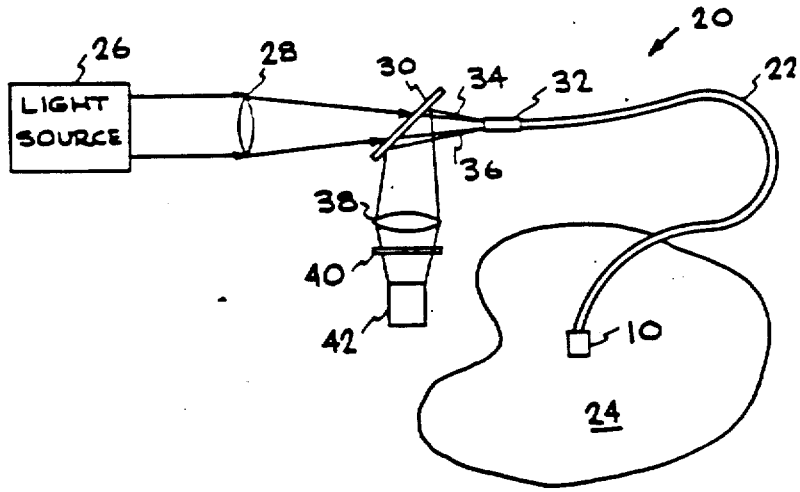

We claim:

1. A fiber optic sensor for differentiating solvents of different refractive index, comprising:
    a fiber optic core;
    a thin film metal clad made of a material selected from platinum, rhodium and palladium formed on and surrounding the fiber optic core of a thickness which modulates the transmission of light through the fiber optic core as a function of the refractive index of a surrounding solvent.

2. The sensor of claim 1 further comprising:
    a reflective tip formed at a tip of the fiber optic core with the thin film clad adjacent to the reflective tip.

3. The sensor of claim 1 further comprising:
    a light source operatively associated with the fiber optic core for inputting a light signal into the core;
    detection means operatively associated with the fiber optic core for detecting a signal from the fiber optic core.

4. The sensor of claim 1 wherein the thin film metal clad is made of platinum.

5. The sensor of claim 1 wherein the thin film metal clad is made of rhodium.

6. The sensor of claim 1 wherein the thin film metal clad is made of palladium.

7. The sensor of claim 1 wherein the metal clad has a thickness of up to about the penetration depth of an evanescent wave propagating through the fiber core.

8. A fiber optic sensor for differentiating solvents of different refractive index, comprising:
    a fiber optic core;
    a thin film metal clad formed on and surrounding the fiber optic core of a thickness such that the transmission of light through the fiber optic core is a function of the refractive index of a surrounding solvent;
    a fluorescent material immobilized at a tip of the fiber optic core with the thin film clad adjacent to the fluorescent tip.

9. The sensor of claim 8 further comprising:
    excitation means for exciting the fluorescent material;
    detection means for detecting a fluorescent signal from the fluorescent material.

10. The sensor of claim 8 wherein the thin film metal clad is made of platinum.

11. The sensor of claim 8 wherein the thin film metal clad is made of a material selected from gold, rhodium and palladium.

12. A method of detecting the refractive index of a solvent, comprising:
    forming a bare fiber optic core;
    forming a thin film metal clad of a material selected from Pt, Au, Rh and Pd on and surrounding the bare fiber optic core of a thickness such that the transmission of light through the fiber optic core is a function of the refractive index of a surrounding solvent;
    contacting the clad with a solvent;
    inputting a light signal into the core;
    detecting decreases in intensity of the inputted light signal after it is transmitted through the core.

13. The method of claim 1 further comprising:
    forming a reflective tip on the fiber core;
    detecting a reflected signal from the core.

14. The method of claim 12 further comprising:
    inputting the light signal at one end of the fiber core;
    detecting a transmitted signal at the other end of the fiber core.

15. A method of detecting the refractive index of a solvent, comprising:
- forming a bare fiber optic core;
- forming a thin film metal clad on and surrounding the bare fiber optic core of a thickness such that the transmission of light through the fiber optic core is a function of the refractive index of a surrounding solvent;
- forming a fluorescent tip on the fiber core;
- contacting the clad with a solvent;
- inputting a light signal into the core of a wavelength selected to excite fluorescence of the tip;
- detecting a fluorescent signal from the core.

16. The method of claim 13 further comprising:
- forming the thin film metal clad of a material selected from Pt, Au, Rh, and Pd.

17. A method of forming a refractive index fiber optic chemical sensor, comprising:
- forming a bare fiber optic core;
- forming a thin film metal clad of a metal selected from Pt, Rh and Pd on and surrounding the bare fiber optic core of a thickness which modulates the transmission of light through the fiber optic core as a function of the refractive index of a surrounding solvent.

18. The method of claim 17 further comprising:
- forming the metal clad by painting the bare core with a metallic paint and heating the painted core.

19. The method of claim 17 further comprising forming the metal clad of Pt.

20. The method of claim 17 further comprising:
- forming the metal clad of a thickness of a few monolayers.

21. The method of claim 17 further comprising forming the metal clad of a thickness of up to about the penetration depth of an evanescent wave propagating through the fiber core.

* * * * *

UNITED STATES PATENT AND TRADEMARK OFFICE
CERTIFICATE OF CORRECTION

PATENT NO. : 4,929,049
DATED : May 29, 1990
INVENTOR(S) : Le Goullon, et al

It is certified that error appears in the above-indentified patent and that said Letters Patent is hereby corrected as shown below:

Title page should be deleted to appear as per attached title page.

Column 4, line 62, "claim 1" should read --claim 12--.

Signed and Sealed this

Twenty-fourth Day of August, 1993

Attest:

BRUCE LEHMAN

*Attesting Officer*   *Commissioner of Patents and Trademarks*

United States Patent [19]

Le Goullon et al.

[11] Patent Number: 4,929,049
[45] Date of Patent: May 29, 1990

[54] FIBER OPTIC REFRACTIVE INDEX SENSOR USING A METAL CLAD

[75] Inventors: Donald Le Goullon, Tracy; Kisholoy Goswami, Walnut Creek; Stanley M. Klainer, San Ramon; Fred P. Milanouich, Lafayette, all of Calif.

[73] Assignee: FiberChem, Inc., Las Vegas, Nev.

[21] Appl. No.: 150,197

[22] Filed: Jan. 29, 1988

[51] Int. Cl.$^5$ .................................................. G02B 6/16
[52] U.S. Cl. ............................... 350/96.29; 350/96.34
[58] Field of Search ........................... 350/96.29–96.34, 350/301; 250/227; 65/3.11, 3.3

[56] References Cited

U.S. PATENT DOCUMENTS

| | | | |
|---|---|---|---|
| 4,418,984 | 12/1983 | Wysocki et al. | 350/96.33 |
| 4,476,870 | 10/1984 | Peterson et al. | 128/634 |
| 4,600,310 | 7/1986 | Cramp et al. | 350/96.29 X |
| 4,695,123 | 9/1987 | Chang et al. | 350/96.29 X |
| 4,781,458 | 11/1988 | Angel et al. | 356/301 |

Primary Examiner—John D. Lee
Assistant Examiner—John Ngo
Attorney, Agent, or Firm—Henry P. Sartorio

[57] ABSTRACT

A refractive index FOCS has a thin metal film clad on a fiber optic core so that transmission through the core is strongly affected by the refractive index of a surrounding solvent. The clad is made of platinum, or also of gold, rhodium or palladium. With a fluorescent tip, the changes in the fluorescent signal are a measure of the solvent refractive index. With a reflective tip, the changes in the reflected signal are measured. In a linear configuration, source and detector are placed at opposite ends of the fiber and changes in the transmitted signal are measured as a function of solvent refractive index.

21 Claims, 2 Drawing Sheets